(12) United States Patent
Chen et al.

(10) Patent No.: US 10,000,541 B2
(45) Date of Patent: Jun. 19, 2018

(54) TRAIL CELL-PENETRATING PEPTIDE-LIKE MUTANT MUR6 AND PREPARATION METHOD THEREOF

(71) Applicant: CHENGDU HUACHUANG BIOTECHNOLOGY CO., LTD, Chengdu, Sichuan (CN)

(72) Inventors: Shouchun Chen, Sichuan (CN); Juan Yan, Sichuan (CN); Qi Xu, Sichuan (CN); Xianzhou Huang, Sichuan (CN); Lijia Wei, Sichuan (CN); Haiyang Hu, Sichuan (CN)

(73) Assignee: CHENGDU HUACHUANG BIOTECHNOLOGY CO., LTD, Chengdu (CN)

( * ) Notice: Subject to any disclaimer, the term of this patent is extended or adjusted under 35 U.S.C. 154(b) by 0 days. days.

(21) Appl. No.: 15/591,144

(22) Filed: May 10, 2017

(65) Prior Publication Data

US 2017/0247424 A1   Aug. 31, 2017

Related U.S. Application Data

(63) Continuation-in-part of application No. PCT/CN2015/073524, filed on Mar. 2, 2015.

(51) Int. Cl.
*C07K 14/525* (2006.01)
*A61K 38/00* (2006.01)

(52) U.S. Cl.
CPC ............ *C07K 14/525* (2013.01); *A61K 38/00* (2013.01)

(58) Field of Classification Search
CPC .... C07K 14/70578; C12N 15/74; C12P 21/02
See application file for complete search history.

(56) References Cited

U.S. PATENT DOCUMENTS 9,102,759 B2 *   8/2015   Pieczykolan .... C07K 14/70575

* cited by examiner

*Primary Examiner* — Robert S Landsman

(57) ABSTRACT

A TRAIL cell-penetrating peptide (CPPs)-like mutant MuR6 and a preparation method and the application thereof. The amino acid sequence of the mutant is SEQ ID NO: 2. The mutant selectively transforms the amino acid coding sequence of No. 114-119 of the outer fragment of the TRAIL wild-type protein cell membrane from VRERGP to RRRRRR, i.e., mutates valine into arginine on the $114^{th}$ coding sequence, glutamic acid into arginine on the $116^{th}$ coding sequence, glycine into arginine on the $118^{th}$ coding sequence and proline into arginine on the $119^{th}$ coding sequence, turning the coding sequence of N-terminal of the mutant protein into that of six arginines and making it a protein containing CPPs-like structure. Having a superior therapeutic effect on different types of tumor, the TRAIL mutant is a new generation of high-efficient drug for inducing tumor apoptosis of much potential.

9 Claims, 4 Drawing Sheets

TRAIL CELL-PENETRATING PEPTIDE-LIKE MUTANT MUR6 AND PREPARATION METHOD THEREOF

CROSS-REFERENCE TO RELATED APPLICATIONS

The present application is a Continuation-in-Part application of PCT application No. PCT/CN2015/073524 filed on Mar. 2, 2015, the contents of which are hereby incorporated by reference.

REFERENCE TO SEQUENCE LISTING

The Sequence Listing is submitted concurrently with the specification as an ASCII formatted text file via EFS-Web, with a file name of "Sequence listing.txt", a creation date of May 9, 2017, and a size of 3,252 bytes. The Sequence Listing filed via EFS-Web is part of the specification and is incorporated in its entirety by reference herein.

TECHNICAL FIELD

The Invention relates to the field of genetic engineering drugs, and particularly to a trail cell-penetrating peptide-like mutant MuR6 and a preparation method and the application thereof.

BACKGROUND ART

1. The Progress and Meaning of Apo2L/TRAIL for Tumor Therapy

Tumor necrosis factor-related apoptosis-inducing ligand (TRAIL) is a member of the superfamily of tumor necrosis factors (TNFs), the gene sequence of which was obtained through independent cloning by Wiley et al. in 1995 and Pitti et al. in 1996; the latter named TRAIL as Apo2 Ligand (Apo2L). Studies later showed that Apo2L and TRAIL are the same kind of protein in nature, therefore, it customarily can be called as Apo2L/TRAIL. TRAIL is firstly used as a conditioning agent for the congenital or acquired immunity of living organisms; then, it plays its role of anti-tumor as the immunological surveillance in the exogenous apoptotic pathway. The greatest benefit of TRAIL is that it can induce apoptosis for various tumors selectively while having hardly any toxicity to normal cells. It is shown from research data that no matter in vitro or in vivo, Apo2L/TRAIL has apoptosis-inducing effect on the human cancer cell lines from various sources, including colon (rectal) cancer, lung cancer, breast cancer, prostatic cancer, pancreatic cancer, renal cancer, CNS tumor, thyroid cancer, lymphoma, leukemia and multiple myeloma, etc.

TRAIL has always been developed as an important potential antineoplastic drug in almost 20 years since it was discovered, the clinical trial of which has entered Phase II in foreign countries and has been finished Phase III in China. A large number of in vitro and in vivo trials verified that TRAIL has tumor specific cytotoxicity and has obvious synergistic effect especially when it is used with small dose of chemotherapy drugs. On the contrary, the studies found that the TRAIL tolerance caused by lack of apoptosis mechanism in living organisms has definite relationship with the rapid growth and transfer of tumor cell.

Tumor is a group of disease with high heterogeneity. The traditional genotyping methods as per tissues and organs and pathologic changes are no longer suitable for tumor diagnosis and treatment. The current research direction is aiming at elucidating genetic expression and molecular subtyping of different tumor cells, so as to provide more targeted treatment to patients. It is realized with better understanding of antineoplastic drugs that, the functioning process of no matter cytotoxic drug, molecular targeted drug or monoclonal antibody involves the activation of tumor cell apoptosis pathway; the signal pathway for inducing apoptosis of tumor cells is the hub and the key link for these drugs to function, and the apoptosis evasion is the critical mechanism for tumor development and drug resistance.

2. Defects and Countermeasures of Apo2L/TRAIL for Tumor Therapy

The recent development shows that it is far from enough to cure various types of tumor with Apo2L/TRAIL only. Although the agonistic monoclonal antibody of recombinant human Apo2L/TRAIL or TRAIL receptor $DR_4/DR_5$ has achieved encouraging results in clinic treatment of Phase I, no definite clinical benefit is showed in the subsequent clinical study of Phase II. A large number of studies show that normal cells and almost more than a half (even 60%) of passage tumor cell strains have shown drug resistance to TRAIL. According to Roberta di peitro and Giorgia zaulim, the antibiotic sensitive rate of Apo2L/TRAIL to 61 strains out of the studied 92 strains of primary or passage tumor cells is 66.3% and the rest 31 strains 33.7%. The tolerance of TRAIL to normal cells has certain physiological significance. Maintaining precise regulation and control effect in vivo, TRAIL only removes the aging, degenerated and transformed cells in the process of growth and development while not killing any normal cells. Almost all TRAIL sensitive tumor cells have similar soundness and functions in each link and factor in the apoptotic signal pathway, while each TRAIL drug-resistant tumor cell has defects and variations in some links and factors in the apoptotic signal pathway. These defects and variations making the apoptotic threshold of the drug-resistant tumor cells increased abnormally, thus the tumor cells can easily escape from apoptosis removal and keep on growing and proliferating.

A large number of studies verified that the independent use of Apo2L/TRAIL does not have significant inhibitory and killing effects to many tumor cells. The reason for that is that the apoptotic signal pathway of tumor cells is a huge and complex system, containing both many apoptosis-inducing factors and a lot of apoptosis inhibitors. The interaction between the two factors determines the final destination of tumor cells. The soundness and function of the apoptotic signal pathway are of necessary condition but not sufficient condition for tumor cell apoptosis. Many different types of drugs, molecules or genetic interference may increase the sensibility of TRAIL to tumor cells. These drugs comprise different types of chemotherapy drugs, natural products and small molecule kinase inhibitors, etc. They strengthen the activity of TRAIL-induced tumor cells apoptosis by strengthening the extracellular apoptotic signal pathway (e.g.: up-regulating death receptors (DRs) expression, enhancing the aggregation and redistribution of DRs in upper lipid raft micro domain of cell membrane, enhancing the endocytosis of TRAIL/DRs compound on the cell membrane, promoting recruitment of TRAIL/DRs complex by DISC, activating the activity of Caspase (Caspase 8) at initial period and inhibiting the activities of apoptosis antagonists as FLIP, XIAP and IAPs) or the mitochondria apoptotic signal pathway (e.g.: strengthening the depolarization of mitochondrial membrane potential, promoting increasing mitochondria permeability and releasing Cyt c, Smac or ARTs, promoting Bid splitting into tBid, promoting oligomerization of Bax and Bad and inhibiting the apoptosis antagonists as Bcl-2, Bcl-xL, Bcl-w, Mcl-1 and Mcl-1) or inhibiting other cell survival signal pathways (such as ERK/PI3K/AKt, MEK, Jak-STAT 3, MAPK and NF-κB) or combining several pathways.

Although the development process of TRAIL and its receptor agonistic monoclonal antibody is frustrated temporally, with fully elucidation of the apoptotic signal pathway, and fully disclosure of the conversion relation of apoptosis and tolerance, the development of targeted ntineoplastic drugs based on apoptotic signal pathway is never stopped. The current studies are mainly focused on combining the application of TRAIL and cytotoxic agent, however most experiments show that such combination will only have obvious synergistic effect on the tumor cell which is relatively sensitive to TRAIL and cannot reverse the resistance caused by various different resistance mechanisms. TRAIL and cytotoxic agent belong to two types of drugs, having differences in drug type, dosage, administration route and mode of action and little possibility for being developed into a new simplex, stable and controlled drug; meanwhile, after TRAIL and cytotoxic agent are combined, the toxic and side effect will still exist, therefore, it has no distinct advantage.

SUMMARY OF THE INVENTION

In order to overcome the defects of the prior art, the Invention is to provide a new type of TRAIL CPPs-like mutant that can significantly increase the TRAIL wild-type protein antineoplastic activity and particularly reverse the drug resistance caused by various drug resistant tumor cells. The prepared mutant protein both can enter the cytoplasm directly by penetrating the cell membrane and take effect rapidly and can promote the aggregation and internalization of DRs/mutant protein complex in the lipid raft micro domain of cell membrane, so as to strengthening the transduction of exogenous apoptotic signal pathway. Having a superior therapeutic effect on different types of tumor, the TRAIL CPPs-like mutant is a new generation of high-efficient drug for inducing tumor apoptosis of much potential.

The technical scheme of the Invention is realized as follows:

A TRAIL CPPs-like mutant, wherein, the amino acid sequence of the mutant is SEQ ID NO: 2.

Further, the mutant selectively transforms the amino acid coding sequence of No. 114-119 of the outer fragment of TRAIL wild-type protein cell membrane, i.e., valine is mutated into arginine on the 114th coding sequence, glutamic acid is mutated into arginine on the 116th coding sequence, glycine is mutated into arginine on the 118th coding sequence and proline is mutated into arginine on the 119th coding sequence, turning the coding sequence of N-terminal of the mutant protein into that of six arginines and making it a protein containing CPPs-like structure.

Further, the cDNA sequence of the mutant is coded as SEQ ID NO: 1.

Further, a kit of the mutant is amplified; the kit comprises the following primers: Upstream primer MuR6-TR-NdeI:

```
Upstream primer MuR6-TR-NdeI:
GGTCATATGCGTCGTCGTCGTCGTCGTCAGCGTGTGGCTGCTCAC
(SEQ ID NO: 3)

Downstream primer TR-Eco-R:
GTTGAATTCT TATTAACCAA CAAGGAAAGC ACCGAAGAAA G
(SEQ ID NO: 4).
```

A preparation method of the TRAIL CPPs-like mutant, comprising the following steps:
(1) Amplification and cloning of cDNA fragment; wherein, the cDNA sequence is SEQ ID NO: 1;
(2) Construction and identification of expression vector;
(3) Fusion expression of recombinant TRAIL protein;
(4) Purification of TRAIL protein;
(5) Identification of TRAIL protein.

As a preferred technical scheme, the construction and identification of expression vector in Step (2) comprises the following steps as:
(a) Excising the sequence of fusion tag in the prokaryotic expression vector;
(b) Cloning the optimized coded TRAIL CPPs-like mutant protein with the cDNA sequence as SEQ ID NO: 1 onto the prokaryotic expression vector to obtain a high-efficient soluble non-fusion expression.

As a preferred technical scheme, the prokaryotic expression vector in Step (b) is pET 32a.

As a preferred technical scheme, during fusion expression of recombinant TRAIL protein in Step (3), the inducing temperature is 18-24° C.

As a preferred technical scheme, the purification of TRAIL protein in Step (4) comprises the following steps as:
Taking cation exchange resin SP Sepharose Fast Flow as the primary purification to capture the target protein from the supernatant after bacteria breaking;
Taking gel chromatography resin Sephadex G-25 medium as the secondary moderate purification to further improve the protein purity and remove the endotoxin; and taking anion exchange resin Q Sepharose Fast Flow as the final polishing purification to meet the requirements of industrialized enlargement and future clinical application.

The application of above TRAIL CPPs-like mutant in preparation of antineoplastic drugs.

Based on the action mechanism of inducing apoptosis of tumor cells in the Invention, TRAIL CPPs-like mutant can enter the tumor cell rapidly through cell penetrating to play its role of inducing cell apoptosis. In addition, TRAIL CPPs-like mutant also can effectively promote the aggregation and redistribution of DRs in micro domain of upper lipid raft of cell membrane and the internalization of TRAIL-DR4/DR5 complex and strengthen the transduction of exogenous apoptotic signal pathway.

The advantages of the Invention are as follows:
1. The Invention provides a brand new protein structure, using the least mutational sites, having the smallest influence on protein structure and obtaining the maximized function. TRAIL CPPs-like mutant only has mutations on four discontinuous mutational sites. The mutation is occurred at the amino terminal of the protein, therefore, it has small influence on biological activity and stability of the protein but obtains the cell penetration ability larger than that of CPPs fusion protein.

2. High proportion of protein expression and soluble expression; using the transformed form of high-efficient prokaryotic expression vector pET32a; the expression vector can obtain the expression level and soluble expression proportion higher than that of TRAIL wild-type protein within the wide induction temperature range of 18-24° C.; the soluble protein proportion is up to 80%-100%.

3. Other than the purification and preparation process of TRAIL wild-type protein, the effectiveness, recovery rate and product quality the process of the Invention are largely improved. As the purification method of affinity chromatography with specificity is not used, the cost for purification is reduced accordingly with significant amplification potential, thus the future clinical needs can be completely met.

4. With wide in vitro biological activity, compared with TRAIL wild-type protein, the antineoplastic activity of TRAIL CPPs-like mutant is largely improved among almost all types of tested tumor cells, and especially has stronger therapeutical effect on the tumor cell strain which is drug-resistant to TRAIL wild-type protein can apparently reverse the tolerance of the cells to TRAIL wild-type protein.

BRIEF DESCRIPTION OF THE DRAWINGS

In order to illustrate the technical schemes in the embodiments of the Invention or in prior art more clearly, the drawings required in description of the embodiments or prior art will be introduced briefly as follows. Obviously, the drawings described below are just a part of the embodiments of the Invention. A person skilled in the art is able to obtain other drawings according to these drawings without any creative work.

DETAILED DESCRIPTION OF THE PREFERRED EMBODIMENTS

Figure 1:
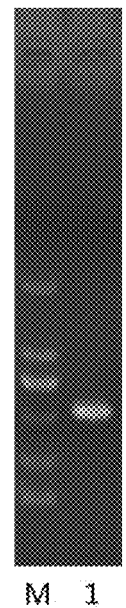
FIG. 1: Electrophoretogram of TRAIL-MuR6 fragment PCR product; electrophoresis conditions: 3% Agarose, voltage: 100 V, 20 min; Lane 1: electrophoretic band of TRAIL-MuR6 fragment PCR product; M: DL2000 (the molecular weights of the band are from top to bottom as 2000 bp, 1000 bp, 750 bp, 500 bp, 250 bp, 100 bp); sample loading amount: 5 μl; sample loading amount of PCR product: 5 μl.

A clear and full description of the technical schemes of the embodiments of the Invention will be given as follows. Obviously, the described embodiments are just a part rather than the whole of the embodiments of the Invention. Based on the embodiments of the Invention, any other embodiments obtained by a person skilled in the art without any creative work will fall within the protection scope of the Invention.

Design Thought of Apo2L/TRAIL CPPs-Like Mutant

The final effective core part of apoptosis protein is within the cell membrane, and the cell membrane is a biological barrier for therapeutic bioactive substance being transferred into cell. The bioactive molecule cannot enter the cell membrane freely due to the hydrophilia of apoptosis protein, thus the function and practical application will be limited. As a kind of positively charged cationic short peptide containing 20-30 amino acids with the function of cell membrane penetration, CPPs is a new technology for drug transportation and delivery that has been developed in recent decades. It is also called protein transduction domain (PTD).

In 1988, Green and Frankel have firstly verified that the trans-activating protein TAT of human immunodeficiency virus (HIV-1) can be transferred into cytoplasm and cell nucleus cross the membrane. One of the TAT polypeptide (GRKKRRQRRRGY) containing rich arginine has the function of cell-penetrating transduction protein, and can mediate various multi-source substances as gene, protein, polypeptide and chemosynthetic nano-particles into cell membrane and even cell nucleus. Later, *drosophila*-homeosis transcription factor ANTP, herpes simplex virus type I (HSV-1), transcription factor VP22, Transpotan and polyarginine sequences were found one after another having the function of cell membrane penetration. At present, hundreds of peptide fragments were found having the function of cell membrane penetration.

The CPPs can be divided into different types according to different standard. At an early stage, CPPs, according to the structural features, have been simply divided into two types as (1) the CPP containing abundant cation with no typic structure, such as TAT and penetratin; (2) amphiphilic a helical peptide from protein signal sequence. According to the sources, CPPs have been divided into two types as natural presence and artificially synthesized and further been divided into three types as (1) CPPs from protein, such as penetratin, TAT and pVEC. They normally have a smallest valid fragment to transport protein, i.e., protein transduction part and membrane ectopic sequence. (2) Model CPPs, such as MAP and Arg (7), which are artificially synthesized for forming a definite amphiphilic a helical peptide or simulating a known CPP structure. The polyarginine and polylysine synthesized according to the CPP structure have a stronger ability of cell membrane penetration than the transduction activity of TAT protein. (3) Artificially designed and synthesized CPPs, such as PEP-1, MPG and Transportan, which are mostly chimeric polypeptides, containing 1 hydrophobic part and 1 hydrophilic part. For example, PEP-1 (KETWW ETWWT EWSQP KKKRK V) contains a fragment full of hydrophobicity tryptophan sequence (KETWW ETWWT EW), a spacer region (SQP) and a region full of hydrophilic lysine sequence (KKKRKV). Such peptide fragment has more advantages. With no need of covalent linkage with target macromolecular, PEP-1 can directly mix with the target macromolecular and then import the protein of native conformation into cells efficiently.

The key structure of the amino acid having a cell-penetrating functional peptide is that the main molecular components are alkaline amino acids such as arginine, lysine and histidine. Alkaline amino acid is a key character of the composition of this kind of cell-penetrating protein. Such amino acid is with strong positive charges, which may have interaction with the cell membrane lipid molecules with negative charge and thus mediate the process of membrane penetration, wherein, the arginine residue plays an important role in protein cellular internalization. At present, there are two points of view with regard to the action mechanism of polyarginine transducing protein into cells as: 1. directly transducing protein into cells through ostioles temporally formed by arginine in the cell membrane and lipid bilayers; 2. transducing protein into cells through cell endocytosis mediated in various forms, including macropinocytosis, caveolin-mediated, clathrin-mediated, phagocytosis and endosome-exchange mechanisms. TRAIL induces the aggregation and redistribution of TRAIL induced DRs in micro domain of upper lipid raft of tumor cell membrane, collects Fas-associated death domain (FADD) and Caspase-8 with or without endocytosis of TRAIL-DR4/5 complex for assembling into a death inducing signaling complex (DISC), and enable the cascade process of apoptotic effect by lysing Caspase-8. Most literatures hold that the internalization of TRAIL-DR4/5 complex is necessary for sustaining amplification of apoptotic signal. Traditionally, foreign protein and CPP are fusion expressed. The expressed fusion protein may change the spatial conformation of protein molecule and thus make it lose biological activity. In addition, the fusion protein increases the biological activity of original protein molecule and brings about safety risks.

Code several amino acids at the N-terminal of amino acid sequence through selective mutation of soluble fragments (114-281aa) of TRAIL protein, make TRAIL form a similar CPPs-like amino acid sequence, i.e., conduct CPPs-like mutation to TRAIL. At present, more than 10 different CPPs-like mutants have been obtained. The Invention breaks through the original design thought of CPP fusion protein, selectively mutates the valine on the $114^{th}$ coding sequence, the glutamic acid on the $116^{th}$ coding sequence, the glycine on the $118^{th}$ coding sequence and the praline on the $119^{th}$ coding sequence into arginine at the N-terminal of the amino acid coding sequence of No. 114-281 of the outer fragment of TRAIL wild-type protein cell membrane, turning the amino acid of No. 114-119 into the sequence of six continuous arginines. The endogenous sequence of six continuous arginines changes the amino acid sequence at the N-terminal of the outer fragment of TRAIL to the minimal extent (maintaining the original $115^{th}$ and $117^{th}$ arginine sequence), maintains the spatial conformation and biological activity of TRAIL protein to the largest extent and structures a sequence of six continuous arginines with the function of membrane penetration. The CPPS-like mutant of the Invention is named as TRAIL-MuR6. CPPs-like mutant is a brand new design thought of a CPP fusion protein.

Embodiment 1

Sequence and Primer Design of TRAIL CPPs-Like Mutant

The mutant selectively transforms the amino acid coding sequence of No. 114-119 of the outer fragment of TRAIL wild-type protein cell membrane from VRERGP to RRRRRR at 4 mutational sites, i.e., mutates valine into arginine on the $114^{th}$ coding sequence, glutamic acid into arginine on the $116^{th}$ coding sequence, glycine into arginine on the $118^{th}$ coding sequence and proline into arginine on the $119^{th}$ coding sequence, turning the coding sequence of N-terminal of the mutant protein into that of six arginines, and making it a protein containing CPPs-like structure.

The cDNA of the coded mutant is SEQ ID NO: 1 and the mutant amino acids SEQ ID NO: 2.

The primers are compounded as follow:

Upstream primer MuR6-TR-NdeI is shown as SEQ ID NO: 3;

Downstream primer TR-Eco-R is shown as SEQ ID NO: 4;

Embodiment 2

PCR Amplifies TRAIL-MuR6 Fragment and Ligates to pET32a; Picking and Identification of Single Colony of Ligation Products Taking pMD19/TRAIL plasmid as a template, PCR mutation amplifies TRAIL-MuR6 fragment. Perform double digests with NdeI and EcoRI respectively to TRAIL-MuR6 target fragment and vector pET32a. Ligate the TRAIL-MuR6 fragment to the vector pET32a with Trx fusion tag sequence excised and transform it into Top10 competent cell; pick monoclone for double enzyme digestion identification with XbaI and EcoRI. Refer to Embodiment 1 for the design of primer. The original sequence of pMD19/TRAIL plasmid is derived from NCBI Reference Sequence: NM_003810.3; the vector pET32a is derived from Invitrogen.

Experimental Procedures

I. PCR Amplifies TRAIL-MuR6 Target Fragment

1. Taking pMD19/TRAIL plasmid as a template, MuR6-TR-NdeI/TR-Eco-R primer pair amplifies TRAIL-MuR6 target fragment. Prepare reaction system according to Table 1; the reaction system is of 50 μl.

TABLE 1

TRAIL-MuR6 PCR reaction system (50 μl)

| Reagent | Reaction system |
|---|---|
| Purified pMD19/TRAIL plasmid | 1 μl |
| 10×Ex Taq Buffer ($Mg^{2+}$ free) | 5 μl |
| dNTP Mix (2.5 mM each) | 4 μl |
| 25 mM $MgCl_2$ | 3 μl |

TABLE 1-continued TRAIL-MuR6 PCR reaction system (50 μl)

| Reagent | Reaction system |
| --- | --- |
| TaKaRa Ex Taq | 1 μl |
| Primer MuR6-TR-NdeI (10 pmol/μl) | 1 μl |
| Primer TR-Eco-R (10 pmol/μl) | 1 μl |
| RNase-Free Water | 34 μl |

2. Collect the solution into the bottom of pipe after briefly centrifugation when vortex shock is blended.

3. Refer to Table 2 for reaction conditions of PCR amplification.

TABLE 2

TRAIL-MuR6 PCR reaction conditions

| Steps | Temperature | Time | |
| --- | --- | --- | --- |
| Predegeneration | 94° C. | 1 min | |
| Degeneration | 94° C. | 15 s | |
| Annealing | 58° C. | 15 s | 25 cycles |
| Extension | 72° C. | 30 s | |
| Final extension | 72° C. | 3 min | |

4. Electrophoresis; take pictures.

5. Conduct gel extraction on the PCR amplified TRAIL-MuR6 target fragment with the Omega Gel Extraction Kit; elute it with 50 μl of ultrapure water; conduct electrophoresis, take pictures; reserve for standby.

II. TRAIL-MuR6 Target Fragment Ligates to pET32a Plasmid after Double Enzyme Digestion 1. Perform double digests on vectors and target gene fragments with NdeI and EcoRI; see table 3 for enzyme digestion system; the reaction system is of 1004

TABLE 3

Double enzyme digestion system of
TRAIL-MuR6 and pET32a (100 μl)

| | Volume | |
| --- | --- | --- |
| Reagent | pET32a plasmid | TRAIL-MuR6 DNA |
| Name of DNA | | |
| DNA | 50 μl | 45 μl |
| NdeI | 5 μl | 3 μl |
| EcoRI | 5 μl | 3 μl |
| 10×H Buffer | 10 μl | 10 μl |
| dH2O | 30 μl | 39 μl |

2. Place the Ep tube into a multi-purpose incubator at 30° C. for 2 hours.

3. Conduct gel extraction with the OMEGA Gel Extraction Kit; elute the vector and the target fragment with 30 μl of ultrapure water. Conduct electrophoresis; take pictures.

4. Ligate the target fragment to the vector after gel extraction; see Table 4 for the ligation system.

TABLE 4

Ligation reaction system of TRAIL-MuR6 and pET32a (10 μl)

| Reagent | Reaction system |
| --- | --- |
| Vector (pET32a) | 1 μl |
| TRAIL-MuR6 | 4 μl |
| Ligase (sol I) | 5 μl |

5. Incubate overnight in metal bath at 16° C.

6. Add 100 μl of Top10 competent cell into 10 μl of ligation product for 30 min of ice-bath.

7. Conduct thermal shock for 90 s in water bath at 42° C.

8. Incubate on ice for 2 min.

9. Add 500 μl of SOC culture medium and conduct shaking cultivation for 45 min at 37° C.

10. After centrifugation of transformed competent cell, discard 400 μl and set aside about 100 μl as culture medium on clean bench. 11. Even the bacteria by blowing, and coat all bacteria on the LB solid medium containing Amp for overnight cultivation at 37° C.

III. Picking of Single Colony and Enzyme Digestion Identification (I) Picking of Single Colony 1. Prepare multiple sterilized test tubes and add 100 ml of ampicillin LB fluid medium into each tube.

2. Put the about 4 ml of culture medium into each test tube.

3. Clamp up sterile tips with the fully burned tweezers and pick up the bacterial colony grown on the plate. Pick 10 bacterial colonies from the pET32a/TRAIL-MuR6 plate. Put the tips into the test tubes with LB culture medium.

4. Tie up each test tube and fasten them on shaking table fixtures. Shake overnight at 37° C., 220 rpm.

(II) Plasmid Extraction

1. Take 1 ml of each bacteria liquid and add it into centrifuge tubes respectively. 10000 g, centrifuge for 1 min; suck out the supernatant as far as possible.

2. Add 250 μl of Solution I (add RNAase A in advance) into the centrifuge tube with bacteria sediment, deposit all suspended bacteria completely.

3. Add with 250 μl of Solution II and blend it gently for fully lysis of bacteria. Then the bacteria liquid becomes clear and thick. Finish this step in 5 min.

4. Add 350 μl of Solution III into the centrifuge tube for blending reversely immediately, then white flocculent sediment appears. 13000 g, centrifuge for 10 min; then sediment is formed at the bottom of centrifuge tube.

5. Equally split the supernatant obtained in Step 5 and put them into two HiBind Miniprep adsorption columns which have been put into collecting pipes. Do not suck out sediment. 10000 g, centrifuge for 1 min; discharge the waste liquid in the collecting pipes and put the adsorption columns back into the collecting pipes.

6. Add 500 μl of Buffer HB into the collecting pipes; 10000 g, centrifuge for 1 min; discharge the waste liquid in the collecting pipes and put the adsorption columns back into the collecting pipes.

7. Add 700 μl of Wash Buffer into the collecting pipes; 10000 g, centrifuge for 1 min; discharge the waste liquid in the collecting pipes and put the adsorption columns back into the collecting pipes.

8. Repeat Step 7.

9. Put the adsorption columns back into the collecting pipes; 13000 g, centrifuge for 2 min; dry the adsorption columns and discharge the waste liquid in the collecting pipes.

10. Place each adsorption column into a new Ep tube of 1.5 ml; drop 65 μl of Elution Buffer into the intermediate section of each adsorption film and place them under ambient temperature for several minutes, above 13000 g, centrifuge for 1 min; collect the plasmid solution into the Ep tube of 1.5 ml.

11. Obtain 60 μl of plasmid DNA each. Store the plasmid under −20° C.

(III) Enzyme Digestion Identification

1. Conduct double enzyme digestion to pET32a/TRAIL-MuR6 plasmid with XbaI and EcoRI. See Table 5 for enzyme digestion reaction system.

TABLE 5

| Enzyme digestion reaction system of pET32a/TRAIL-MuR6 (10 µl) | |
|---|---|
| Reagent | Volume |
| pET32a/TRAIL-Mu3 plasmid | 5 µl |
| XbaI | 0.5 µl |
| EcoRI | 0.5 µl |
| 10×M Buffer | 1 µl |
| dH2O | 3 µl |

2. Place the Ep tube into a multi-purpose incubator at 37° C., incubate for 2 hours.

3. Conduct electrophoresis identification after enzyme digestion.

(IV) Select the Correctly Enzyme Digested and Successfully Ligated Strain, Preserve in with Glycerin and Send it for Sequencing.

Experiment Results

I. Result of PCR amplified target fragment

Amplify the TRAIL-MuR6 target fragment amplified through mutation by MuR6-TR-NdeI/TR-Eco-R primer pair; the molecular weight of the fragment is about 500 bp, as shown in FIG. 1; obtain the target gene according to the above PCR reaction conditions.

Figure 2:
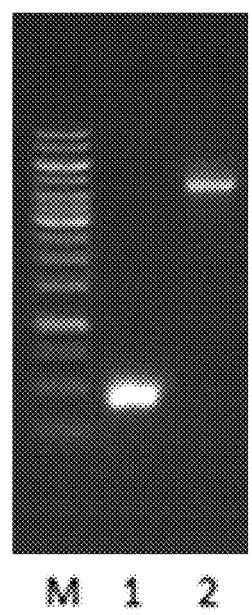
FIG. 2: Electrophoretogram of TRAIL-MuR6 and pET32a plasmid NdeI, EcoRI after enzyme digestion; electrophoresis conditions: 1% Agarose, voltage: 150 V, 25 min; Lane 1: gel extraction electrophoretic band of TRAIL-MuR6 after enzyme digestion; Lane2: gel extraction electrophoretic band of pET32a after enzyme digestion; M: GeneRuler1 kb DNA Ladder (the molecular weights of the band are from top to bottom as 10000 bp, 8000 bp, 6000 bp, 5000 bp, 4000 bp, 3500 bp, 3000 bp, 2500 bp, 2000 bp, 1500 bp, 1000 bp, 750 bp, 500 bp, 250 bp); sample loading amount: 5 μl; sample loading amount of PCR product: 3 μl.

II. Theoretically, after double enzyme digestion to TRAIL-MuR6 and pET32a with NdeI and EcoRI, the target fragments of about 500 bp and 5.4 kb are obtained, as shown in FIG. 2. A single band is obtained as expected through gel extraction after enzyme digestion.

III. Results of ligation and transformation between TRAIL-MuR6 target fragment and pET32a 1. Bacterial colony grows with normal density in the plate.

2. As for the picked single colony, partial test tubes are grown with bacteria of normal density on the next day.

Figure 3:
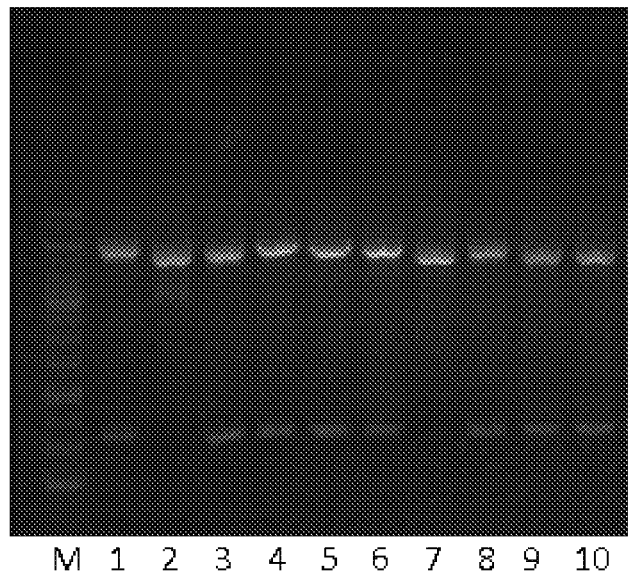
FIG. 3: Electrophoretogram of pET32a/TRAIL-MuR6 plasmid XbaI, EcoRI after enzyme digestion identification; electrophoresis conditions: 1% Agarose, voltage: 150 V, 30 min; Lane 1-10: Electrophoretogram of plasmid extracted by pET32a/TRAIL-MuR6 strain after enzyme digestion; M: GeneRuler1 kb DNA Ladder (the molecular weights of the band are from top to bottom as 10000 bp, 8000 bp, 6000 bp, 5000 bp, 4000 bp, 3500 bp, 3000 bp, 2500 bp, 2000 bp, 1500 bp, 1000 bp, 750 bp, 500 bp, 250 bp); loading amount of verified product: 10 μl; loading amount of Marker: 5 μl.

3. Identify plasmid through enzyme digestion; identify pET32a/TRAIL-MuR6 plasmid through double enzyme digestion with XbaI and EcoRI; the vector fragment of about 5.4 Kb and the target fragment of about 550 bp should be obtained after successful ligation of plasmid and enzyme digestion. As shown in FIG. 3, 8 samples of pET32a/TRAIL-MuR6 are positive; send the positive plasmids to BGI for sequencing. Save the strains from the plasmids with correct sequence.

Embodiment 3 pET32a/TRAIL-MuR6 Expression Test

Select a single bacterium from the plasmid transformed competent *e. coli* BL21 (DE3) with correct sequence obtained in Embodiment 2 for expression test to inspect the effect of expression.

Experimental Procedures

I. Plasmid Transformation and Strain Preservation

1. Prepare a LB culture medium of 100 ml and sterilize it at 121° C. for 20 min.

2. Take 1 µl of pET32a/TRAIL-MuR6 plasmid and add it into the BL21 (DE3) competent cell for 30 min of ice-bath.

3. Conduct thermal shock for 90 s in water bath at 42° C.

4. Incubate on ice for 3 min.

5. Take 20 µl of transformed competent cell and coat on the LB solid medium containing Amp for overnight cultivation at 37° C.

6. After plate is grown with bacterial colonies, select a single bacterium from the plate and add it into 50 ml of LB (Amp$^+$) for overnight cultivation at 37° C.

7. Save 20 pipes of glycerin bacteria with a final concentration of glycerin as 15% at −20° C.

II. Strain Expression

1. Take 1000 µl of each overnight cultivated pET32a/TRAIL-MuR6 culture solution for inoculating into 50 ml of LB (Amp$^+$) culture medium. The temperature after inoculation is 37° C.; conduct shaking cultivation for 3 h at 250 rpm and lower the temperature to 24° C. Add 0.1 M of IPTG as per the proportion of 1% for induction cultivation. Before induction, take a sample of 0.5 ml and discard the supernatant through centrifugation; add 50 µl of H$_2$O and then add 50 µl of 2×loading buffer after weight drop to prepare a sample of post-induction electrophoresis.

2. Collect the bacteria after overnight induction, detect A$_{600}$ value; take a sample of 150 µl and discard the supernatant through centrifugation; add 50 µl of H$_2$O and then add 50 µl of 2×loading buffer after resuspension to prepare a sample of post-induction electrophoresis; centrifuge the rest bacteria solution at 12000 rpm for 5 min with the 5430R-type centrifugal machine.

3. Take 50 ml of culture solution and obtain the bacteria through centrifugation; conduct resuspension with 8 ml of 50 mM Na$_2$HPO$_4$ solution for bacteria breaking with ultrasonic wave. Conditions for bacteria breaking: Φ6 probe; 200 W pulse bacteria breaking for 2 s and suspended for 2 s for a circulation of 10 min.

4. Take 1 ml of bacteria breaking liquid for 10 min of centrifugation at 12000 rpm; separate the supernatant and the sediment; conduct resuspension for the sediment with 1 ml of H$_2$O; take 20 µl of each supernatant and sediment resuspension solution and add with 30 µl of H$_2$O and 50 µl of 2×loading buffer for preparing the electrophoresis sample.

5. Place the prepared electrophoresis sample into boiling water bath for 10 min of treatment; using a 5430R-type centrifugal machine with A-45-30-11 type rotor; after centrifugation at 12000 rpm for 10 min; take 10 µl of supernatant for electrophoresis.

Experiment Results

Figure 4:
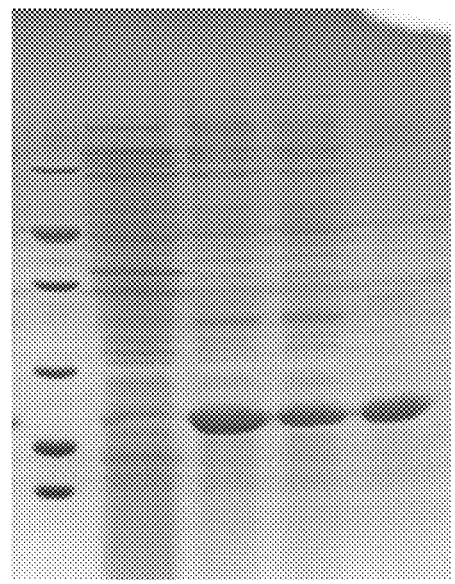
FIG. 4: SDS-PAGE electrophoretogram of pET32a/TRAIL-MuR6 expression; electrophoresis conditions: 15% gel; voltage: 200 V, 35 min; Lane 1: electrophoretic band of pET32a/TRAIL-MuR6 before induction; Lane 2: electrophoretic band of pET32a/TRAIL-MuR6 after induction; Lane 3: Supernatant electrophoretic band of pET32a/TRAIL-MuR6 after bacteria breaking; Lane 4: Sediment electrophoretic band of pET32a/TRAIL-MuR6 after bacteria breaking; M: Unstained Protein Molecular Weight Marker (the molecular weights of the band are from top to bottom as 116.0 KDa, 66.2 KDa, 45.0 KDa, 35.0 KDa, 25.0 KDa, 18.4 KDa, 14.4 KDa); loading amount of Marker: 5 μl; loading amount of other sample: 20 μl.

See FIG. 4 for the experimental electrophoregram (pET32a/TRAIL-MuR6). TRAIL-MuR6 has strong expression and the most expression product is in the supernatant after bacteria breaking; the proportion of soluble expression is high.

Embodiment 4

Purification Preparation of TRAIL-MuR6 Protein

After abundant exploration to lab scale process of TRAIL-MuR6, TRAIL-MuR6 protein purification process is established. TRAIL-MuR6 protein is purified in batch through a three-step approach as SP Sepharose Fast Flow gel chromatographic column, Sephadex G-25 medium chromatographic column and anion exchange penetration for obtaining internal and external activity analysis of sample donor.

Experimental Procedures

I. Breaking and Centrifugation of Bacteria

1. Take 70 g of MuR6 bacteria, add $Na_2CO_3$, glycerin, Tween80, DTT and NaCl, and add $H_2O$ to achieve a total volume of 400 ml, keeping the final concentration of the above substances at 20 mM $Na_2CO_3$, 5% glycerin, 0.1% Tween80.1 mM DTT and 500 mM NaCl.

2. Conduct ultrasonic bacteria breaking to the bacteria liquid. Conditions for bacteria breaking: Φ10 probe; 500 W pulse bacteria breaking for 2 s and suspended for 2 s for a circulation of 15 min.

3. Use a 5430R-type centrifugal machine with F-35-6-30 type rotor; after centrifugation at 7850 rpm for 40 min, take supernatant for filtration with a filter membrane of 0.45 μm and take it as an upper column sample.

II. Preparation of Protein Purification Solution and Column

1. The following solutions should be prepared:

(1) Cation exchange buffer A: 20 mM $Na_2CO_3$-$NaHCO_3$, 0.5 M NaCl, 5% glycerin, 0.1% Tween80, 1 mM DTT and adjust the pH value to 10.50.

(2) Cation exchange buffer B: 20 mM $Na_2CO_3$-$NaHCO_3$, 1.5 M NaCl, 5% glycerin, 0.1% Tween80, 1 mM DTT and adjust the pH value to 10.20.

(3) 0.5 M NaOH.

(4) 2 M NaCl.

(5) Desalination and anion exchange buffer: 0.15 MNaCl, 0.3 M glycine and 0.2 M arginine.

2. Use SP Sepharose Fast Flow gel chromatographic column; use 5 CV of pure water to wash the residual ethyl alcohol on the column and then equilibrate it with 5 CV of corresponding equilibration buffer.

3. Use Sephadex G-25 medium gel chromatographic column; use 5 CV of pure water to wash the residual ethyl alcohol on the column and then equilibrate it with 5 CV of anion exchange buffer.

4. Use Q Sepharose Fast Flow gel chromatographic column; use 5 CV of pure water to wash the residual ethyl alcohol on the column and then equilibrate it with 5 CV of anion exchange buffer.

III. Cation Exchange and Purification

Conduct cation exchange and purification as per the following steps. Collect all penetration and elution compositions during purification for electrophoretic analysis:

1. Equilibration: equilibrate SP Sepharose Fast Flow chromatographic column with cation exchange buffer A until UV is stabilized.

2. Sample preparation and sample loading: take the centrifugal supernatant of broken bacterium and load the sample.

3. Cleaning: clean the column with 2 CV of cation exchange buffer A to remove the residual uncombined protein.

4. Elution: elute the impure protein with 2 CV of 10% of cation exchange buffer B and elute the target protein with 2 CV of 100% of cation exchange buffer B.

5. NaOH cleaning: clean the column with 2 CV of 0.5 M NaOH solution.

6. Reequilibration: reequilibrate the column with 5 CV of cation exchange buffer A.

IV. Anion Exchange and Purification

Conduct the second step of anion exchange and purification as per the following steps. Collect all penetration and elution compositions during purification for electrophoretic analysis:

1. Equilibration: equilibrate Q Sepharose Fast Flow chromatographic column with anion exchange A buffer until UV is stabilized.

2. Sample preparation and sample loading: take cation exchange purified and eluted sample, load the sample after the buffer solution is displaced to anion exchange buffer through Sephadex G-25 medium chromatographic column.

3. Cleansing of equilibrium liquid: clean the column with 2 CV of anion exchange buffer to obtain the target protein uncombined onto the column.

4. NaCl cleaning: clean the column with 2 CV of 2 M NaCl to remove the protein combined onto the column.

5. NaOH cleaning: clean the column with 2 CV of 0.5 M NaOH solution.

6. Reequilibration: reequilibrate the column with anion exchange buffer.

Experiment Results

Figure 5:
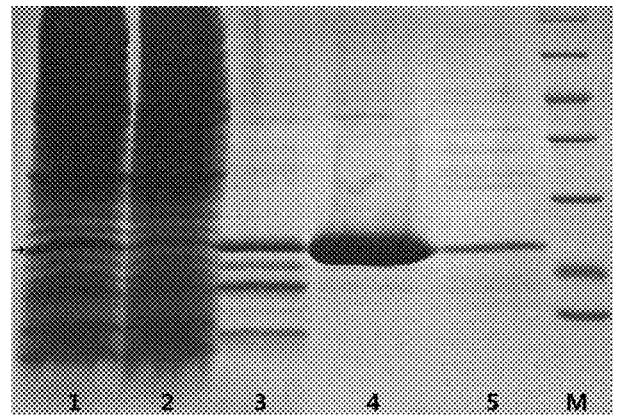
FIG. 5: SDS-PAGE electrophoretogram of cation exchange process; electrophoresis conditions: 15% gel; voltage: 200V, 50 min; Lane 1: Cation exchange stoste; Lane 2: Cation exchange penetrating fluid; Lane 3: Cation exchange 600 mM NaCl eluent; Lane 4: Cation exchange 1.5 M NaCl eluent; Lane 5: Cation exchange NaOH eluent; M: Unstained Protein Molecular Weight Marker (the molecular weights of the band are from top to bottom as 116.0 KDa, 66.2 KDa, 45.0 KDa, 35.0 KDa, 25.0 KDa, 18.4 KDa, 14.4 KDa). loading amount of Marker: 5 μl; loading amount of other sample: 20 μl.
Figure 6:
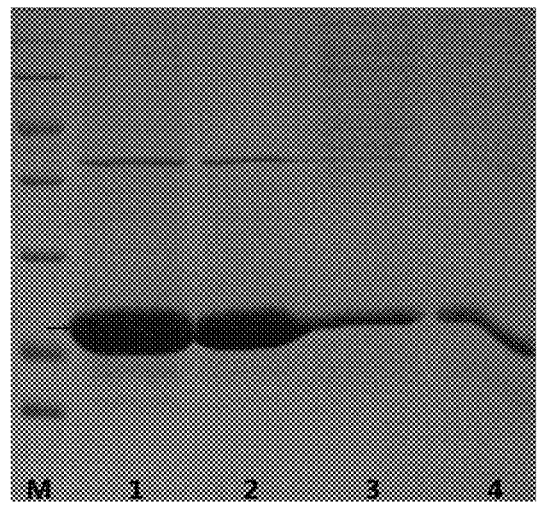
FIG. 6: SDS-PAGE electrophoretogram of anion exchange process; electrophoresis conditions: 15% gel; voltage: 200 V, 50 min; Lane 1: Anion exchange stoste; Lane 2: Anion exchange penetrating fluid; Lane 3: 2 M NaCl eluent; Lane 4: 0.5 M NaOH eluent; M: Unstained Protein Molecular Weight Marker (the molecular weights of the band are from top to bottom as 116.0 KDa, 66.2 KDa, 45.0 KDa, 35.0 KDa, 25.0 KDa, 18.4 KDa, 14.4 KDa); loading amount of Marker: 5 μl; loading amount of other sample: 20 μl.

See FIGS. 5 and 6 for the electrophoretic results of the sample at each step of purification process: in step 1 the eluent collected is 26 ml with a concentration of 7.727 mg/ml; upon detection the purity of the target protein is 82.45%; in step 2 the desalinated eluent is 34 ml with a concentration of 3.870 mg/ml, which can remove the residual impure protein and partial pyrogen; in step 3, the anion exchange penetrating fluid is 51 ml with a concentration of 2.332 mg/ml, which is mainly used to remove pyrogen. Repeat the experimental operations in the Embodiment to obtain the protein of 193.93 mg, which is enough for in vitro biological activity evaluation Embodiment 6

Western Blot Detection of TRAIL-MuR6 Protein

Because TRAIL-MuR6 is obtained by mutation of 4 sites at the N-terminal of wild-type TRAIL, the antigenic determinant of TRAIL is still remained and can be specifically bound to the polyclonal antibody of TRAIL. Therefore, the polyclonal antibody of TRAIL can be used for detection and identification.

Experimental Procedures

I. Sample Preparation

1. After the TRAIL-MuR6 protein purified in Embodiment 5 is unfrozen from −20° C., dilute it to 1 mg/ml with ultrapure water according to the provided concentration. Take 50 μl of sample and add 50 μl of 2×loading buffer to prepare an electrophoresis sample. Take 10 μl of electrophoresis, i.e., the amount of sample loading is 5 ug.

2. Dissolve the reference substance TRAIL-20131204 dried frozen aquatic products (prepared in laboratory and compared with NIBSC international standard substan; the activity is more than $10^7$ IU/mg) with 1 ml of PBS; take 50 μl of sample and add 50 μl of 2×loading buffer to prepare an electrophoresis sample. Take 10 μl of electrophoresis, i.e., the sample loading amount is 5 ug.

II. Detection Process

After electrophoretic separation with 15% of SDS-PAGE, transfer the sample to the PVDF membrane. Close it at 4° C. for overnight firstly and incubate it with primary antibody

[rabbit-anti-human TRAIL polyclonal antibody (1:500)] under ambient temperature for 2 hours; then incubate it with secondary antibody [goat-anti-rabbit IgG-HRP (1:5000)] under ambient temperature for 2 hours; then detect it through enhance chemiluminescence (ECL). The specific steps are as follows:

1. Separate protein with 15% of SDS-PAGE electrophoretically; take out the gel, cut off the edge and immerse it into the TBST buffer for 15 min.

2. Transfer membrane with PVDF membrane (wet transferring): soak the PVDF membrane with methyl alcohol for 15 s before use; immerse it into the distilled water for 1-3 min and then equilibrate it in membrane transferring buffer; pave sponge mat, filter paper (4-8 pieces), target glue, PVDF membrane, filter paper (4-8 pieces) and sponge mat in membrane transferrin clamp successively from cathode to anode; fasten the clamp after bubble is exhausted and put it in the membrane transferring slot at the voltage of 40 V for 45 min.

3. Closing membrane: close the membrane in confining liquid (3% BSA) at 4° C. for overnight; take it out on the next day and shake it for 30 min under ambient temperature so as to close the nonspecific binding sites.

4. Primary antibody incubation: dilute the confining liquid for primary antibody to a working concentration [rabbit-anti-human TRAIL polyclonal antibody (1:500)] and shake it with the membrane and incubate it under ambient temperature for 2 hours.

5. Membrane cleansing: clean the membrane with washing membrane for three times, 10 min for each time. The membrane of 10×10 cm needs more than 50 ml of cleaning solution.

6. Secondary antibody incubation: dilute the HRP-marked confining liquid for secondary antibody to a working concentration [goat-anti-rabbit IgG-HRP (1:5000)] and shake it with the membrane and incubate it under ambient temperature for 2 hours.

7. Membrane cleansing: clean the membrane with washing membrane for three times, 10 min for each time. The membrane of 10×10 cm needs more than 50 ml of cleaning solution.

8. Coloration: (1) mix the Solution A and Solution B of the same volume to prepare mixed liquid enough for detection (0.125 ml/cm$^2$). Use the mixed liquid for detection immediately after preparation. It can remain stable within 1 hour under ambient temperature. (2) Drain off the redundant cleaning solution on the blotting membrane but do not dry the membrane. Add the mixed liquid for detection on one side of the membrane which contains protein, drain off the redundant mixed liquid and put the membrane on the Image Station 4000R of Kodak gel imaging for exposure with X-ray. Select 1 min for the first time of exposure and adjust the time of exposure according to the imaging result. Record the image with computer.

9. Result judgment: positive result should show obvious colored tape. Negative result shows no color.

Experiment Results

Figure 7:
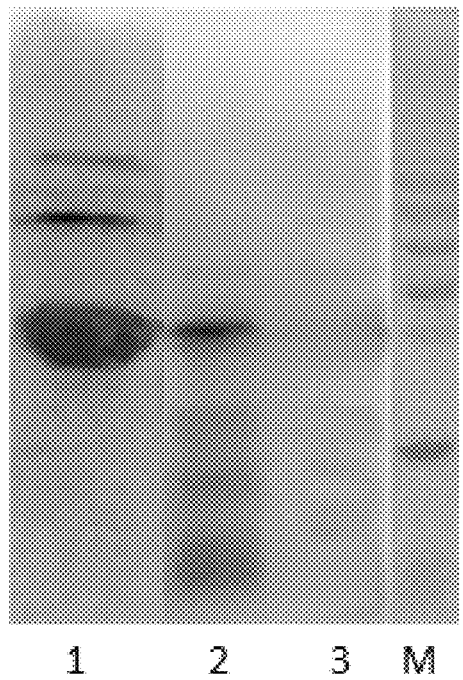
FIG. 7: Result of western blot identification; Lane 1: Result of TRAIL-MuR6western blot; Lane 2: Result of TRAILwestern blot; M: PageRuler Prestained Protein Ladder (the molecular weights of the band are from top to bottom as 170 KDa, 130 KDa, 100 KDa, 70 KDa, 55 KDa, 40 KDa, 35 KDa, 25 KDa, 15 KDa, 10 KDa).

As shown in FIG. 7, TRAIL-MuR6 and TRAIL reference substance are showing positive results and the negative control is showing negative reaction.

Embodiment 7

Protein TRAIL-MuR6 and TRAIL Bioactivity Analysis

Detect the in vitro anti-proliferative activity IC50 value of 2 protein samples as TRAIL-MuR6 and wide-type TRAIL to 12 tumor cell strains with CCK-8 detection kit and evaluate the in vitro bioactivity.

Materials and Methods

The cell strains for detection are all from Shanghai Institute of Biochemistry and Cell Biology or Wuhan Institute of Virology of the Chinese Academy of Sciences Wuhan Institute of Virology

| | Cell type | Cell strain | Source |
|---|---|---|---|
| 1 | Pancreatic cancer (3) | BxPC-3 | Purchased from Shanghai Institute of Biochemistry and Cell Biology |
| 2 | | CFPAC-1 | Purchased from Shanghai Institute of Biochemistry and Cell Biology |
| 3 | | PANC-1 | Purchased from Shanghai Institute of Biochemistry and Cell Biology |
| 4 | Lung cancer (2) | A549 | Purchased from Wuhan Institute of Virology |
| 5 | | NCI-H460 | Purchased from Shanghai Institute of Biochemistry and Cell Biology |
| 6 | Colon cancer (3) | HCT116 | Purchased from Shanghai Institute of Biochemistry and Cell Biology |
| 7 | | HT-29 | Purchased from Wuhan Institute of Virology |
| 8 | | SW620 | Purchased from Shanghai Institute of Biochemistry and Cell Biology |
| 9 | Breast cancer (3) | MCF-7 | Purchased from Wuhan Institute of Virology |
| 10 | | MDA-MB-231 | Purchased from Wuhan Institute of Virology |
| 11 | | T47D | Purchased from Wuhan Institute of Virology |
| 12 | Acute t lymphocytic leukemia (1) | Jurkat | Purchased from Wuhan Institute of Virology |

Reagents and Consumables
Cell Counting Kit-8 (Cat# CK04-13, Dojindo)
96-well culture plate (Nest Biotech Co)
Fetal calf serum (Code: FS101-02, TransGen)
Culture medium (purchased from GIBCO)
Desktop microplate reader Infinite F50 (TECAN)
2 protein samples: prepared through Embodiment 5 or in laboratory.

Experimental Procedures

1. Preparation of Reagent
Preparation of Culture Medium

| | Cell type | Cell strain | Culture medium and conditions | Inoculum density |
|---|---|---|---|---|
| 1 | Pancreatic cancer (3) | BxPC-3 | RPMI-1640 + 10% FBS + 1.0 mM sodium pyruvate; $CO_2$, 5%; 37.0° C. | $4 \times 10^3$/well |
| 2 | | CFPAC-1 | IMEM (GIBCO Art. No.: 1460614) + 10% FBS; $CO_2$, 5%; 37.0° C. | $7 \times 10^3$/well |
| 3 | | PANC-1 | Low glucose DMEM + 10% FBS; $CO_2$; 5%; 37.0° C. | $5 \times 10^3$/well |

| Cell type | Cell strain | Culture medium and conditions | Inoculum density |
|---|---|---|---|
| 4 Lung cancer (2) | A549 | Low glucose DMEM + 10% FBS; $CO_2$; 5%; 37.0° C. | $5 \times 10^3$/well |
| 5 | NCI-H460 | RPMI-1640 + 10% FBS; $CO_2$, 5%; 37.0° C. | $8 \times 10^3$/well |
| 6 Colon cancer (3) | HCT116 | McCoy's 5a Medium Modified (GIBCO Art. No.: 1459946) + 10% FBS; $CO_2$, 5%; 37.0° C. | $4 \times 10^3$/well |
| 7 | HT-29 | Low glucose DMEM + 10% FBS; $CO_2$, 5%; 37.0° C. | $5 \times 10^3$/well |
| 8 | SW620 | Leibovitz's L-15 + 10% FBS; without $CO_2$; 37° C. | $8 \times 10^3$/well |
| 9 Breast cancer (3) | MCF-7 | Low glucose DMEM (GIBCO Art. No.: 11443791) + 0.01 mg/ml bovine insulin; FBS, 10%; $CO_2$, 5%; 37.0° C. | $8 \times 10^3$/well |
| 10 | MDA-MB-231 | Leibovitz's L-15 (GIBCO Art. No.: 1466860) + 10% FBS; without $CO_2$; 37° C. | $8 \times 10^3$/well |
| 11 | T47D | RPMI-1640 + 10% FBS + 0.2 Units/ml bovine insulin; $CO_2$, 5%; 37.0° C. | $10 \times 10^3$/well |
| 12 Acute t lymphocytic leukemia (1) | Jurkat | RPMI-1640 Medium (GIBCO Art. No.: 31800022); FBS, 10%; $CO_2$, 5%; 37.0° C. | $5 \times 10^4$/well |

Preparation of Protein Samples

Dilute the 2 protein samples with sterile PBS buffer to achieve a final concentration of 5 mg/ml and conduct filtration and sterilization.

2. IC50 Experiment a) Collect logarithmic cells in growing period, count the number and re-suspend the cells with complete medium, adjust the cell concentration to an appropriate one (determined by the result of cell density optimization experiment), inoculate with 96-well plate and add 100 µl of cell suspension in each well. Incubate the cell (except SW620, with no need for 5% of $CO_2$) in an incubator for 24 hours at 37° C., relative humidity of 100% and 5% of $CO_2$.

b) Dilute the protein samples to be measured with sterile PBS buffer to 5 mg/ml, then conduct gradient dilution for 8 times and add cells as per 25 µl/well. From 1 mg/ml to 0, the final concentration of the compound is diluted in a gradient of three-times, involving 10 concentration points; then adjust the action final concentration for the protein samples according to the primary experiment results.

c) Incubate the cell (except SW620, with no need for 5% of $CO_2$) in an incubator for 48 hours at 37° C., relative humidity of 100% and 5% of $CO_2$.

d) Suck to discard the culture medium, add the complete medium containing 10% of CCK-8 in the incubator at 37° C. for incubation for 2-4 hours.

e) After gently shaking, determinate the absorbance at the wave length of 450 nm on SpectraMax M5 Microplate Reader, take the absorbance at 650 nm for reference and calculate the inhibition ratio.

3. Data Processing

Calculate the inhibition ratio of the drug to tumor cell growth as per the following formula:

Inhibition ratio of tumor cell growth %=[(Ac−As)/(Ac−Ab)]×100%

As: OA/RLU of sample (cell+CCK-8+compound to be measured)
Ac: OA/RLU of negative control (cell+CCK-8)
Ab: OA/RLU of positive control (culture medium+CCK-8)

Use the software Graphpad Prism 5 and the formula as log (inhibitor) vs. normalized response-Variable slope for IC50 curve fitting and calculate the value of IC50.

Experiment Results

The experiment tested the in vitro anti-cell proliferative activities of 2 protein samples (TRAIL-MuR6 and wild-type TRAIL) to 3 pancreatic cancer cell strains (CFPAC-1, BxPC-3 and PANC-1), 2 lung cancer cell strains (NCI-H460, A 549), 3 colon (rectal) cancer cell strains (SW620, HT-29, HCT 116), 3 breast cancer cell strains (MDA-MB-231, MCF-7, T47D) and 1 acute T lymphocytic leukemia cell strains (Jurkat). The results are as follows:

Comparison of IC50 values of 12 tumor cells (µg/mL)

| | Cell type | Cell strain | TRAIL-MuR6 | TRAIL |
|---|---|---|---|---|
| 1 | Pancreatic | BxPC-3 | 0.0046 | >100 |
| 2 | cancer (3) | CFPAC-1 | 0.0811 | >100 |
| 3 | | PANC-1 | 0.0078 | >100 |
| 4 | Lung | A549 | 0.0085 | >100 |
| 5 | cancer (2) | NCI-H460 | 0.00365 | 0.002 |
| 6 | Colon | HCT116 | 0.003 | 0.015 |
| 7 | cancer (3) | HT-29 | 0.0359 | >100 |
| 8 | | SW620 | 0.0012 | 0.008762 |
| 9 | Breast | MCF-7 | 0.0036 | >100 |
| 10 | cancer (3) | MDA-MB-231 | 0.003 | 0.003 |
| 11 | | T47D | 0.0273 | >100 |
| 12 | Acute t lymphocytic leukemia (1) | Jurkat | 0.0018 | |

Experiment Results

Compared with TRAIL wild-type protein, the antineoplastic activity of TRAIL CPPs-like mutant TRAIL-MuR6 is largely improved among almost all types of tested tumor cells [including multiple colon (rectal) cancer cells, multiple lung cancer cells, multiple pancreatic cancer cells and multiple breast cancer cells], and especially has stronger therapeutical effect on the tumor cell strain which is drug-resistant to TRAIL wild-type protein and can apparently reverse the tolerance of the cells to TRAIL wild-type protein.

The above are the preferred embodiments rather than the limitations of the Invention. Any amendment, equivalent replacement and improvement made within the range of the spirit and rule of the Invention shall be included in the protection scope of the Invention.

The invention claimed is:

1. A tumor necrosis factor-related apoptosis-inducing ligand (TRAIL) cell-penetrating peptide (CPPs)-like mutant, wherein the mutant has an amino acid sequence as set forth in SEQ ID NO: 2.

2. The TRAIL CPPs-like mutant according to claim 1, wherein a cDNA sequence of the TRAIL CPPs-like mutant is coded as set forth in SEQ ID NO: 1.

3. A kit for amplifying the TRAIL CPPs-like mutant according to claim 2, wherein the kit comprises the following primers:

```
Upstream primer MuR6-TR-NdeI:
                                        (SEQ ID NO: 3)
GGTCATATGCGTCGTCGTCGTCGTCAGCGTGTGGCTGCTCAC Downstream primer TR-Eco-R:
                                        (SEQ ID NO: 4)
GTTGAATTCT-TATTAACCAA-CAAGGAAAGC-ACCGAAGAAA-G.
```

4. A method for preparing a tumor necrosis factor-related apoptosis-inducing ligand (TRAIL) cell-penetrating peptide (CPPs)-like mutant, comprising the following steps:
(a) amplifying and cloning a cDNA fragment; wherein the cDNA fragment has a sequence as set forth in SEQ ID NO: 1;
(b) constructing and identifying an expression vector;
(c) expressing the TRAIL CPPs-like mutant;
(d) purifying the TRAIL CPPs-like mutant;
(e) identifying the TRAIL CPPs-like mutant.

5. The method according to claim 4, wherein the constructing and identifying the expression vector in Step (b) comprises the following steps:
(i) excising nucleotides of a fusion tag sequence in a prokaryotic expression vector;
(ii) cloning the sequence of the cDNA fragment as set forth in SEQ ID NO: 1 into the prokaryotic expression vector to obtain a high-efficient soluble non-fusion expression.

6. The method according to claim 5, wherein the prokaryotic expression vector in Step (ii) is pET 32a.

7. The method according to claim 4, wherein, during the expressing the TRAIL CPPs-like mutant in Step (c), an inducing temperature is 18-24° C.

8. The method according to claim 4, wherein the purifying the TRAIL CPPs-like mutant in Step (d) comprises the following steps:
(i) using a cation exchange resin as a primary purification to capture the TRAIL CPPs-like mutant from a supernatant after bacteria breaking;
(ii) using a gel chromatography resin medium as a secondary purification to further improve purity of the TRAIL CPPs-like mutant and remove an endotoxin; and
(iii) using an anion exchange resin as a final polishing purification to meet requirements of industrialized amplification and future clinical application.

9. An antineoplastic drug comprising the TRAIT, CPPs-like mutant according to claim 1.

* * * * *

SEQUENCE LISTING

<160> NUMBER OF SEQ ID NOS: 4

<210> SEQ ID NO 1
<211> LENGTH: 510
<212> TYPE: DNA
<213> ORGANISM: Artificial Sequence
<220> FEATURE:
<221> NAME/KEY: misc_feature
<222> LOCATION: (1)..(510)
<223> OTHER INFORMATION: cDNA of the coded mutant

<400> SEQUENCE: 1

```
atgcgtcgtc gtcgtcgtcg tcagcgtgtg gctgctcaca tcactggtac tcgtggtcgt      60
tctaacactc tttcttctcc gaactctaaa acgaaaaag ctcttggtcg taaaatcaac       120
tcttgggaat cttctcgttc tggtcactct ttcctttcta accttcacct tcgtaacggt      180
gaacttgtta tccacgaaaa aggtttctac tacatctact ctcagactta cttccgtttc     240
caggaagaaa tcaaagaaaa cactaaaaac gataaacaga tggttcagta catctacaaa     300
tacacctctt acccggaccc gatccttctt atgaaatctg ctcgtaactc ttgctggtct     360
aaagatgctg aatacggtct ttactctatc taccagggtg gtatcttcga acttaaagaa     420
aacgatcgta tcttcgtttc tgttactaac gaacacctta tcgatatgga tcacgaggct     480
tctttcttcg gtgctttcct tgttggttaa                                     510
```

<210> SEQ ID NO 2
<211> LENGTH: 169
<212> TYPE: PRT
<213> ORGANISM: Artificial Sequence
<220> FEATURE:
<221> NAME/KEY: artificial sequence
<222> LOCATION: (1)..(169)
<223> OTHER INFORMATION: mutant amino acid sequence

<400> SEQUENCE: 2

```
Met Arg Arg Arg Arg Arg Gln Arg Val Ala Ala His Ile Thr Gly
1               5                   10                  15

Thr Arg Gly Arg Ser Asn Thr Leu Ser Ser Pro Asn Ser Lys Asn Glu
            20                  25                  30

Lys Ala Leu Gly Arg Lys Ile Asn Ser Trp Glu Ser Ser Arg Ser Gly
        35                  40                  45

His Ser Phe Leu Ser Asn Leu His Leu Arg Asn Gly Glu Leu Val Ile
    50                  55                  60

His Glu Lys Gly Phe Tyr Tyr Ile Tyr Ser Gln Thr Tyr Phe Arg Phe
65                  70                  75                  80

Gln Glu Glu Ile Lys Glu Asn Thr Lys Asn Asp Lys Gln Met Val Gln
                85                  90                  95

Tyr Ile Tyr Lys Tyr Thr Ser Tyr Pro Asp Pro Ile Leu Leu Met Lys
            100                 105                 110

Ser Ala Arg Asn Ser Cys Trp Ser Lys Asp Ala Glu Tyr Gly Leu Tyr
        115                 120                 125

Ser Ile Tyr Gln Gly Gly Ile Phe Glu Leu Lys Glu Asn Asp Arg Ile
    130                 135                 140

Phe Val Ser Val Thr Asn Glu His Leu Ile Asp Met Asp His Glu Ala
145                 150                 155                 160

Ser Phe Phe Gly Ala Phe Leu Val Gly
                165
```

<210> SEQ ID NO 3

```
<211> LENGTH: 45
<212> TYPE: DNA
<213> ORGANISM: Artificial Sequence
<220> FEATURE:
<221> NAME/KEY: misc_feature
<222> LOCATION: (1)..(45)
<223> OTHER INFORMATION: Upstream primer MuR6-TR -NdeI

<400> SEQUENCE: 3
ggtcatatgc gtcgtcgtcg tcgtcgtcag cgtgtggctg ctcac          45

<210> SEQ ID NO 4
<211> LENGTH: 41
<212> TYPE: DNA
<213> ORGANISM: Artificial Sequence
<220> FEATURE:
<221> NAME/KEY: misc_feature
<222> LOCATION: (1)..(41)
<223> OTHER INFORMATION: Downstream primer TR-Eco-R

<400> SEQUENCE: 4
gttgaattct tattaaccaa caaggaaagc accgaagaaa g              41
```